US011166718B2

(12) United States Patent
Sgroi, Jr. et al.

(10) Patent No.: US 11,166,718 B2
(45) Date of Patent: Nov. 9, 2021

(54) ILLUMINATED DELIVERY SYSTEM FOR ANVIL ASSEMBLIES

(71) Applicant: Covidien LP, Mansfield, MA (US)

(72) Inventors: Anthony Sgroi, Jr., Wallingford, CT (US); Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 156 days.

(21) Appl. No.: 16/533,854

(22) Filed: Aug. 7, 2019

(65) Prior Publication Data

US 2020/0085429 A1 Mar. 19, 2020

Related U.S. Application Data

(60) Provisional application No. 62/731,120, filed on Sep. 14, 2018.

(51) Int. Cl.
| | |
|---|---|
| *A61B 17/072* | (2006.01) |
| *A61B 17/115* | (2006.01) |
| *A61B 90/30* | (2016.01) |
| *A61B 17/00* | (2006.01) |

(52) U.S. Cl.
CPC ........ *A61B 17/072* (2013.01); *A61B 17/1155* (2013.01); *A61B 90/30* (2016.02); *A61B 2017/00292* (2013.01); *A61B 2017/00734* (2013.01); *A61B 2017/07257* (2013.01)

(58) Field of Classification Search
CPC .... A61B 17/072; A61B 17/1155; A61B 90/30
USPC .................................... 227/179.1; 606/108
See application file for complete search history.

(56) References Cited

U.S. PATENT DOCUMENTS

| | | | | |
|---|---|---|---|---|
| 5,395,030 | A | * | 3/1995 | Kuramoto .......... A61B 1/00087 227/179.1 |
| 8,109,426 | B2 | | 2/2012 | Milliman et al. |
| 8,403,942 | B2 | * | 3/2013 | Milliman ........... A61B 17/1155 606/108 |
| 9,517,070 | B2 | * | 12/2016 | Mulreed ............ A61B 17/0469 |
| 2004/0087977 | A1 | * | 5/2004 | Nolan ................. A61B 17/115 606/142 |
| 2006/0229643 | A1 | | 10/2006 | Nolan et al. |
| 2007/0088389 | A1 | | 4/2007 | Dunkin et al. |
| 2015/0351621 | A1 | | 12/2015 | Hill et al. |
| 2017/0000475 | A1 | | 1/2017 | Sgroi, Jr. et al. |

OTHER PUBLICATIONS

European Search Report dated Jan. 8, 2020, issued in EP Appln. No. 19197176, 8 pages.
European Communication dated Nov. 4, 2020, corresopnding to counterpark European Application No. 19197176.1; 3 pages.

* cited by examiner

*Primary Examiner* — Nathaniel C Chukwurah
(74) *Attorney, Agent, or Firm* — Carter, DeLuca & Farrell LLP

(57) ABSTRACT

A delivery system for trans-oral insertion of an anvil assembly is provided. The anvil delivery system includes a flexible tube configured for trans-oral insertion into a patient, and a light assembly disposed within the flexible tube configured to emit a light.

16 Claims, 6 Drawing Sheets

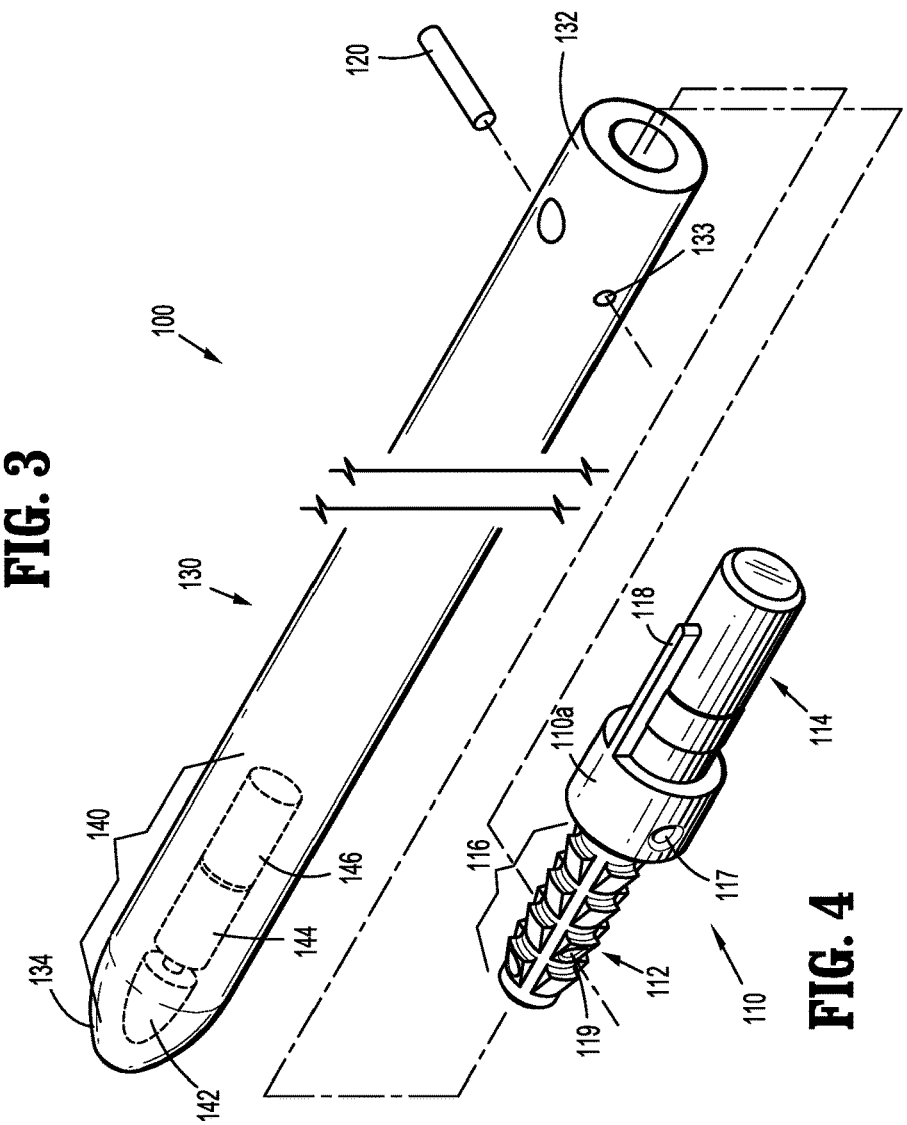
FIG. 3
FIG. 4

ILLUMINATED DELIVERY SYSTEM FOR ANVIL ASSEMBLIES

CROSS-REFERENCE TO RELATED APPLICATIONS

This application claims the benefit of and priority to U.S. Provisional Patent Application Ser. No. 62/731,120 filed Sep. 14, 2018, the entire disclosure of which is incorporated by reference herein.

BACKGROUND

Technical Field

The present disclosure relates to delivery systems for anvil assemblies. More particularly, the present disclosure relates to a trans-oral delivery system for anvil assemblies.

Background of Related Art

Trans-oral delivery systems for delivering an anvil assembly to a surgical site, e.g., the stomach, typically include a tubular guide that is secured to the anvil assembly with an adapter. The tubular guide is inserted through the mouth, fed down the esophagus, and into the stomach of the patient. The guide member is received in the abdominal cavity through an incision in the stomach.

Locating the guide member and directing the guide member through an incision in the stomach can be a complicated and time consuming process. It would be beneficial to have a guide member that facilitates locating the distal end of the guide member within the stomach.

SUMMARY

An anvil delivery system is provided. The anvil delivery system includes a flexible tube configured for trans-oral insertion into a patient, and a light assembly disposed within the second end of the flexible tube configured to emit a light. The flexible tube includes a first end and a second end. The delivery system may include an adapter assembly secured to the flexible tube. The adapter assembly may be configured to secure an anvil assembly to the flexible tube.

In embodiments, the delivery assembly includes an anvil assembly secured to the adapter assembly. The light assembly may include a light source, a power source, and a switch assembly. The light source may include a light emitting diode. In embodiments, the light source includes a plurality of light emitting diodes. The power source may include a battery. The switch assembly may include a pressure switch. The second end of the flexible tube may be rounded. The second end of the flexible tube may include a cap. The first end of the flexible tube may be open and the second end of the flexible tube may be closed.

Also provided is a method of trans-oral insertion of an anvil assembly into a patient. The method includes activating a light source of a light assembly disposed within a first end of a flexible tube of a delivery system such that a light emanates from a first end of the flexible tube, inserting the first end of the flexible tube into a mouth and down an esophagus of a patient and into a stomach of the patient, viewing the light emanating from the first end of the flexible tube within the stomach of the patient, creating an incision in the stomach of the patient in proximity to the light emanating from the first end of the flexible tube, and receiving the first end of the flexible tube through the incision in the stomach.

In embodiments, the method may further include securing an anvil assembly to the flexible tube. Activating the light source may include squeezing the flexible tube to toggle a pressure switch to an on position.

BRIEF DESCRIPTION OF THE DRAWINGS

Various embodiments of the presently disclosed anvil assembly and anvil assembly delivery system are disclosed herein with reference to the drawings wherein:

FIG. 3 is a top view of the anvil delivery system shown in FIG. 1;

FIG. 4 is a perspective view of a flexible tube and an adapter assembly of the anvil delivery system shown in FIG. 1;

DETAILED DESCRIPTION OF EMBODIMENTS

Figure 2:
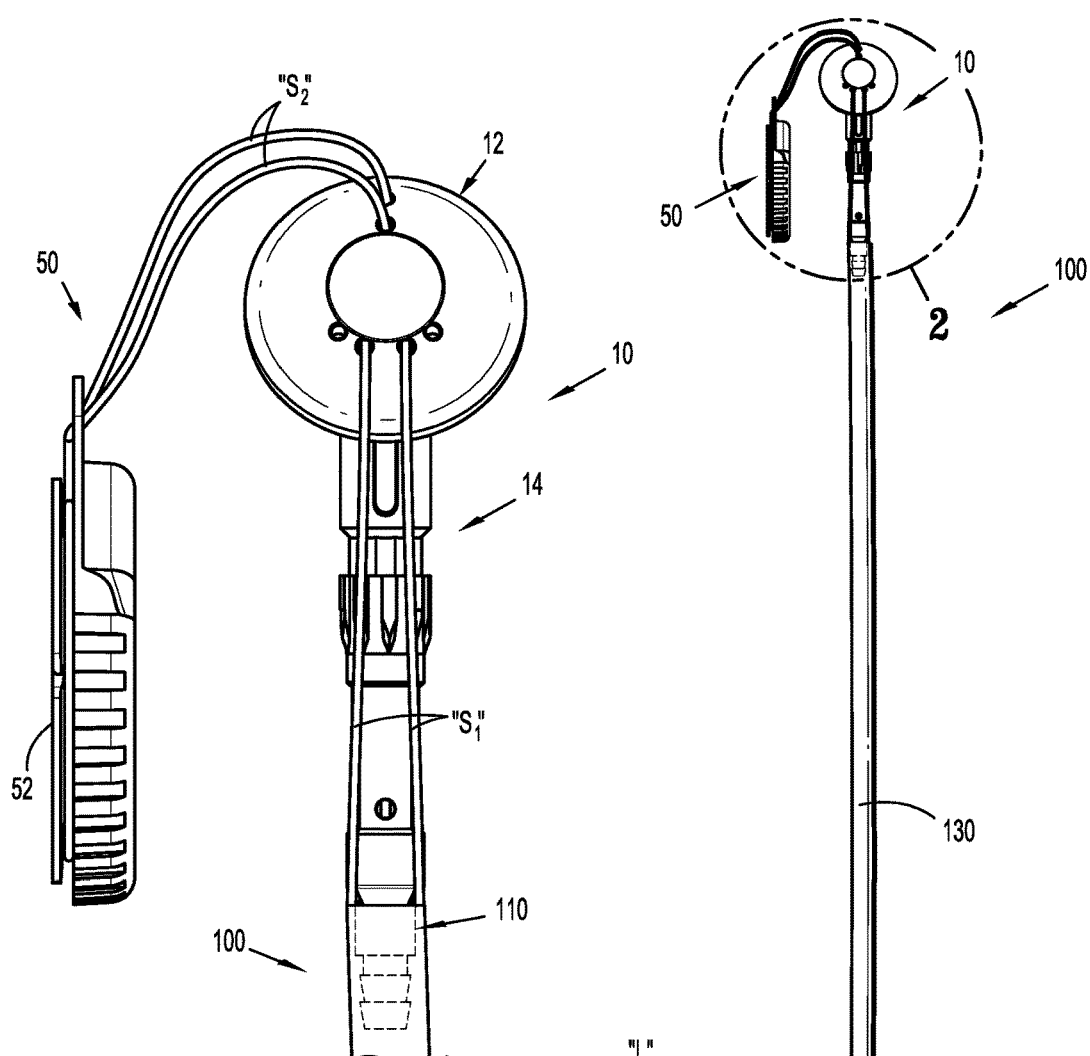
FIG. 2 is an enlarged area of detail indicated in FIG. 1.

Embodiments of the presently disclosed anvil assembly delivery system will now be described in detail with reference to the drawings in which like reference numerals designate identical or corresponding elements in each of the several views. Throughout this description, the term "proximal" will refer to the portion of the instrument closest to the operator and the term "distal" will refer to the portion of the instrument furthest from the operator.

Figure 1:
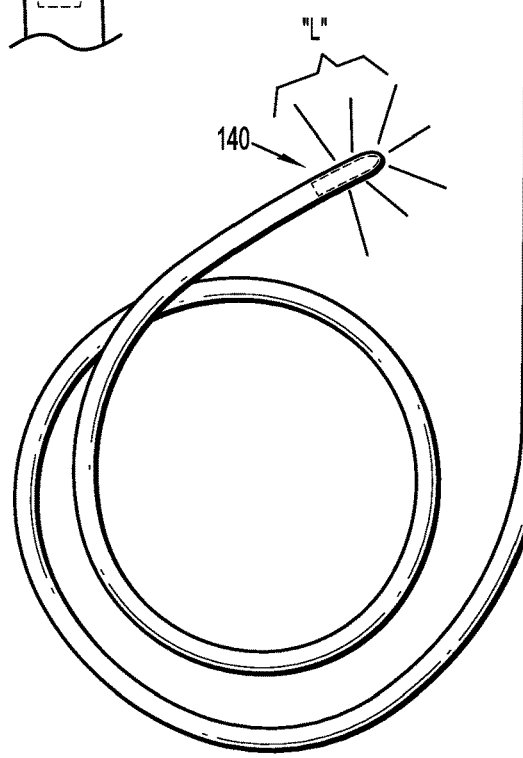
FIG. 1 is a perspective view of an anvil delivery system according to the present disclosure including an anvil assembly and reel assembly secured thereto.

FIG. 1 illustrates an anvil delivery system according to the present disclosure shown generally as delivery system 100. The delivery system 100 is shown including an anvil assembly 10 and reel assembly 50 secured the delivery system 100. Although the aspects of the present disclosure will be described with reference to the anvil assembly 10 and the delivery system 100, it is envisioned that the aspects of the present disclosure may be modified for use with any trans-oral delivery system.

The anvil assembly 10 and the reel assembly 50 will only be described to the extent necessary to fully disclose the aspects of the present disclosure. For a detailed description of an exemplary anvil assembly, please refer to commonly owned U.S. Pat. No. 8,109,426 ("the '426 patent") and U.S. Pat. No. 9,517,070 ("the '070 patent"), the contents of which are incorporated by reference herein in their entirety. For a detailed description of an exemplary reel assembly, please refer to the '070 patent.

With particular reference to FIG. 2, the anvil assembly 10 includes a head assembly 12 pivotally secured to a center rod assembly 14. The head assembly 12 is pivotal relative to the center rod assembly 14 between a first tilted position (FIG.

2), an operative position (not shown), and a second tilted position (not shown). The head assembly 12 of the anvil assembly 10 is retained in the first tilted position (as shown) to facilitate trans-oral insertion of the anvil assembly 10 into a patient. The anvil assembly 10 is maintained in the first tilted position by a retaining suture "S1". For exemplary methods of retaining a head assembly of an anvil assembly in the first tilted position, please refer to the '426 patent and the '070 patent, the contents of which were previous incorporated herein, and to commonly owned U.S. Pat. App. Pub. No. 2017/0000475 ("the '475 publication)", the content of which is incorporated by reference herein in its entirety.

As shown in FIG. 2, a retrieval suture "S2" of the reel assembly 50 is secured to the head assembly 12 of the anvil assembly 10. More particularly, the retrieval suture "S2" of the reel assembly 50 is secured to the head assembly 12 of the anvil assembly 10 and is received about a reel member 52 of the reel assembly 50. During trans-oral insertion of the anvil assembly 10, the retrieval suture "S2" of the reel assembly 50 unwinds from the reel 52 as the delivery system 10 is fed through the mouth and through the esophagus of a patient. The retrieval suture "S2" permits trans-oral retrieval of the anvil assembly 10 from within the patient in the event of a patient emergency, e.g., heart attack, or malfunction of the surgical equipment. The retrieval suture "S2" may also be used to dislodge or assist in guiding the anvil assembly 10 to a surgical site.

With reference now to FIGS. 3-6, the delivery system 100 includes an adapter member 110 and a flexible tube or member 130. The adapter member 110 facilitates connection of the anvil assembly 10 (FIG. 3) with the flexible tube 130.

With particular reference to FIG. 4, the adapter member 110 of the delivery system 100 includes a first end 112 configured to be received within the open end 132 of the flexible tube 130 and a second end 114 configured to be received within a bore 15 (FIG. 2) of the center rod 14 (FIG. 2) of the anvil assembly 10. The first end 112 includes a series of annular rings 116 configured to frictionally secure the first end 112 of the adapter member 110 within the open end 132 of the flexible tube 130. The second end 114 of the adapter member 110 includes an alignment feature 118 to properly position the adapter member 110 relative to the anvil assembly 10.

The adapter member 110 defines a first throughbore 117 in a central hub portion 110a thereof and a second throughbore 119 in the first end 112 thereof. Depending on the suture tie-down method used to retain the head assembly 12 (FIG. 2) of the anvil assembly 10 (FIG. 2) in the first tilted position, the first throughbore 117 may be used to receive the retaining suture "S2". The second throughbore 119 aligns with a throughbore 133 formed in the open end 132 of the flexible tube 130. Receipt of a locking pin 120 through the second throughbore 119 of the adapter member 110 and the throughbore 133 of the flexible tube 130 secures the adapter member 110 with the flexible tube 130. For a detailed description of the structure and function of exemplary adapter members, please refer to the '426 and '070 patents and the '475 publication.

Still referring to FIGS. 3-6, the flexible tube 130 includes an open end 132 (as mentioned above) and a closed end 134. The flexible tube 130 is configured facilitate insertion of the anvil assembly 10 (FIG. 2) into and through the mouth and the esophagus of a patient and position the anvil assembly 10 within the stomach of the patient. The open end 132 of the flexible tube 130 is configured to support the adapter member 110 and the anvil assembly 10. As noted above, a throughbore 133 is defined in the flexible tube 130 distal of the open end 132 and is configured to receive the locking pin 120 to secure the adapter assembly 110 to the flexible tube 130. The flexible tube 130 may define one or more throughbores (not shown) for accommodating the retaining suture "S2" used to secure the head assembly 12 of the anvil assembly 10 in the first tilted position (FIG. 2).

The closed end 134 of the flexible tube 130 of the delivery system 100 is configured to facilitate trans-oral receipt of the flexible tube 130 and attached anvil assembly 10 into a patient. The closed end 134 may be formed as a separate cap (not shown) that is secured to the flexible tube 130. Alternatively, the flexible tube 130 may be melted, molded, or otherwise formed to create the closed end 134. The closed end 134 includes a rounded, blunt, or semi-spherical shape.

At least the portion of the flexible tube 130 disposed adjacent the closed end 134 of the flexible tube 130 is formed from a transparent or translucent material. In this manner, light "L" from a light source 140 disposed within the flexible tube 130 is visible through the flexible tube 130. In embodiments, the flexible tube 130, in its entirety, is composed from the same transparent or translucent material. Alternatively, the cap (not shown) affixed to the flexible tube 130 is transparent or translucent. In other embodiments, the flexible tube 130 includes a window or windows, e.g., slits, openings (not shown), formed in or near the closed end 134 through which the light "L" from the light assembly 140 is visible.

Figure 5:
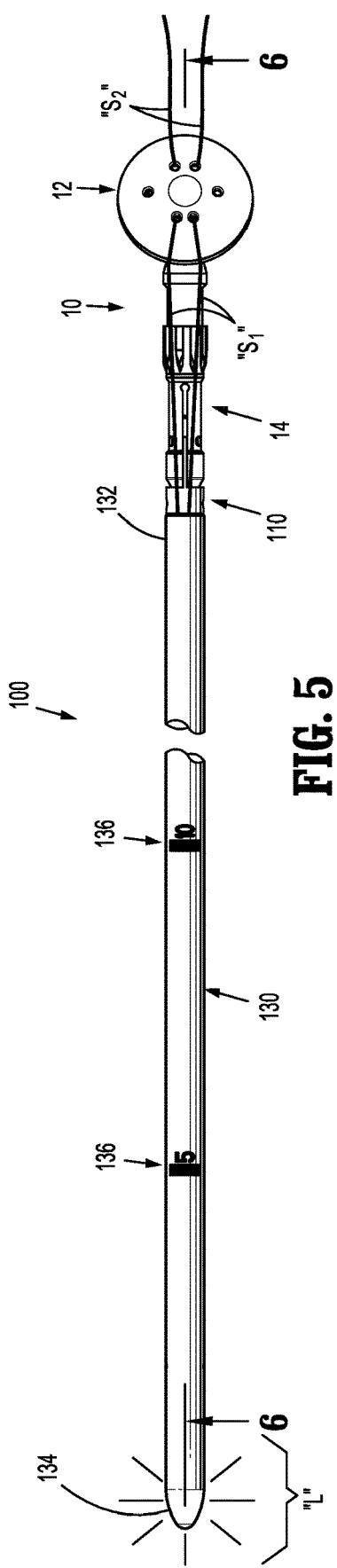
FIG. 5 is a top view of the anvil delivery system with attached anvil assembly shown in FIG. 1.

With particular reference now to FIG. 5, the flexible tube 130 of the delivery system 100 may include markings or other gradations 136 along the length thereof to indicate to a surgeon how much of the flexible tube 130 has been received within the patient during insertion and/or to indicate the length of the flexible tube 130 remaining in the patient upon removal.

Figure 6:
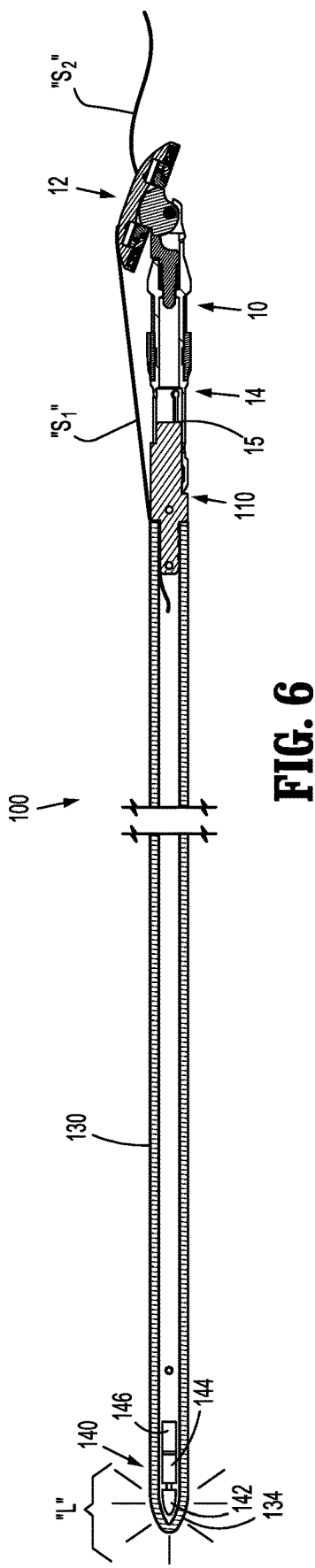
FIG. 6 is a cross-sectional side view taken along line 6-6 shown in FIG. 5.

With particular reference to FIGS. 4 and 6, the light assembly 140 of the delivery system 100 is disposed within the closed distal end 134 of the flexible tube 130. The light assembly 140 includes a light source 142, a source of power 144 for powering the light source 142, and a switch assembly 146 for activating the light source 142. In embodiments, the light source 142 is a light emitting diode (LED), however, the use of other light emitting elements is envisioned. For example, the light source 142 may include a chemiluminescent material, e.g., glow stick, that is activated immediately prior to use. The light source 142 may produce a light "L" of any color and/or intensity. It is envisioned that that the light "L" produced by the light source 142 may be blinking or otherwise adjusted to facilitate locating of the closed end 134 of the flexible tube 130. In embodiments, the light source 142 may include a plurality of light sources spaced along the flexible tube 130. For example, the light sources 142 may be spaced at one inch (1") increments along the flexible tube 130.

The power source 144 of the light assembly 140 may include any suitable battery. The switch assembly 146 may include a pressure switch that may be toggled on and off by squeezing the flexible tube 130. Alternatively, the switch assembly 146 may include an on off switch or button. It is envisioned that the light assembly 140 may not include a switch assembly, and instead, includes an interrupter (not shown) positioned between the light source 142 and the power source 144 to prevent contact between the light source 142 and the power source 144. In this manner, the light source 142 is activated by removing the interrupter. In embodiments, the interrupter includes a strip of non-conductive material that may be removed by a surgeon to activate the light source 142.

The light assembly 140 of the delivery system 100 may be press-fit within the flexible tube 130. Alternatively, the light assembly 140 may be secured within the flexible tube 130 using adhesive, welding, fasteners, or with any other suitable method. The light assembly 140 may be received within the flexible tube 130 prior to the closed end 134 being closed. Alternatively, the light assembly 140 is received within the flexible tube 130 through the open end 132 of the flexible tube 130 prior to the adapter assembly 110 being secured to the flexible tube 130.

Although the power source 144 of the light assembly 140 is shown disposed adjacent the closed end 134 of the flexible tube 130, the power source 144 may be disposed anywhere along the flexible tube 130. For example, the power source 144 may be disposed within the adapter member 110. Alternatively, the power source 144 may be mounted external of the flexible tube 130. Similarly, the switch assembly 146 may be disposed anywhere along the flexible tube 130, within the adapter member 140, or external of the flexible tube 110.

Figure 7:
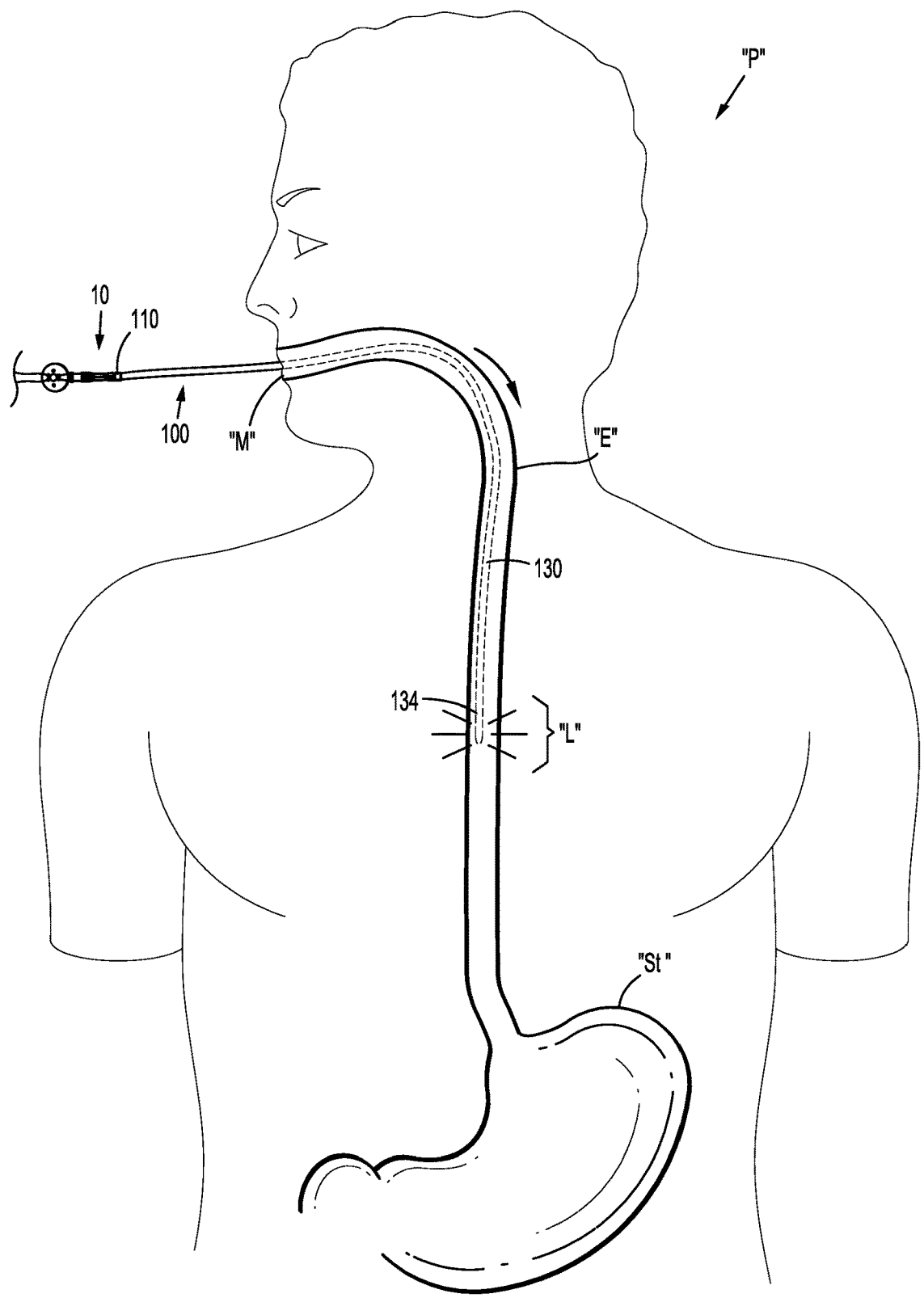
FIG. 7 is an illustration of the anvil delivery system of FIG. 1 inserted into a mouth and down an esophagus of a patient.
Figure 8:
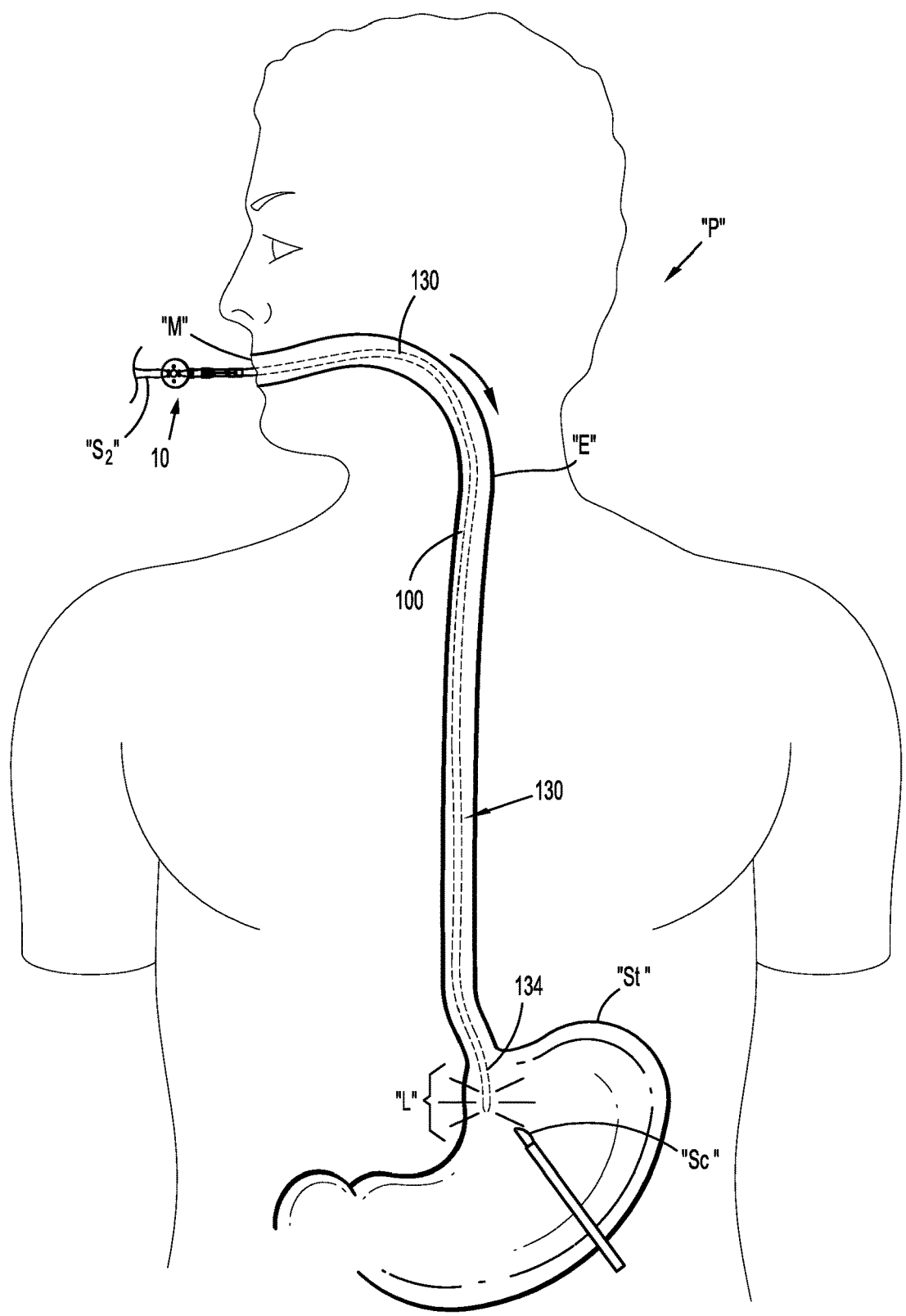
FIG. 8 is an illustration of the anvil delivery system of FIG. 1 received in the stomach of the patient.
Figure 9:
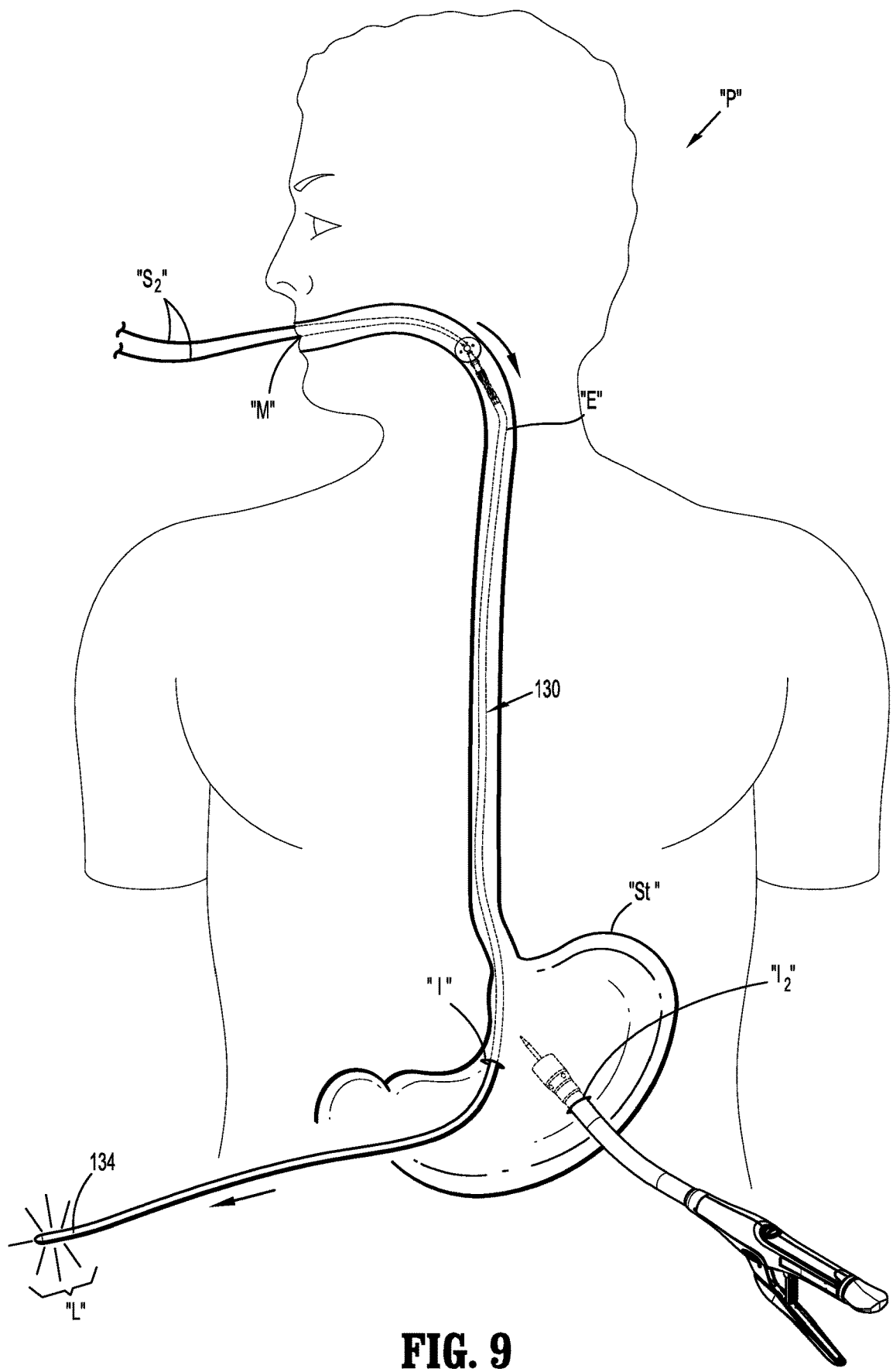
FIG. 9 is an illustration of the anvil delivery system of FIG. 1 received through an incision in the stomach of the patient.

With reference now to FIGS. 7-9, methods for delivering the anvil assembly 10 to a surgical site within a patient utilizing the delivery system 100 will be described. In one method, the anvil assembly 10 is provided to a surgeon in the first tilted position supported on the anvil delivery system 100 and ready for use. Alternatively, the surgeon secures the anvil assembly 10 to the anvil delivery system 100 in the manner described in any of the '426 and '070 patents, or the '475 publication.

Once the anvil assembly 10 is secured to the flexible tube 130, the surgeon activates the light source 142 of the light assembly 140 disposed within the flexible tube 130 to provide light "L" adjacent the closed end 134 of the flexible tube 130. As described above, in embodiments, the light assembly 140 includes the switch assembly 146 having a pressure switch (not shown) that may be toggled on by squeezing the flexible tube 130. Alternatively, the switch assembly 130 may include an on/off switch or button that may be turned on by the surgeon.

The surgeon next inserts the closed end 134 of the flexible tube 130 of the delivery system 100 into the mouth "M" of the patient "P" and moves the flexible tube 130 down through the esophagus "E" of the patient "P" to a surgical site, e.g., the stomach "St". As the flexible tube 130 is fed down the esophagus "E" and into the stomach "St", the light "L" emanating from the light assembly 140 in the closed end 134 of the flexible tube 130 may be viewed by the surgeon. At any point during the anvil assembly insertion procedure, the abdominal cavity of the patient "P" may be darkened to facilitate viewing of the light "L" emanating from the closed end 134 of the flexible tube 130.

Once the light "L" emanating from the closed end 134 of the flexible tube 130 is located within the stomach "St", the surgeon makes an incision "I" at the surgical site (stomach "St" as shown) to create an inner access to the closed end 134 of the flexible tube 130. The surgeon then pulls the closed end 134 of the flexible tube 130 through the incision "I". The flexible tube 130 is pulled through the incision "I" until the center rod 14 of the anvil assembly 10 is received through the incision "I". When the anvil assembly 10 is properly positioned at the surgical site, the surgeon may release the anvil delivery system 100 from the anvil assembly 10 by cutting the retaining suture "S1" (FIG. 2) and separating the anvil assembly 10 from the adapter member 110.

The surgical stapling procedure may then be completed as described in any of the '426 and '070 patents, and the '475 publication.

It is envisioned that the delivery system 100 may be configured to be sterilized and reused. The light assembly 140, in its entirety, and/or the power source 144 of the light assembly 140, may be removable and replaceable.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil delivery system comprising:
   a flexible tube configured for trans-oral insertion into a patient, the flexible tube including a first end and a second end, the second end being configured to secure an anvil assembly thereto; and
   a light assembly disposed within the second end of the flexible tube, the light assembly being configured to emit a light, the light assembly including a light source and a switch assembly for activating the light source.

2. The system of claim 1, further including an anvil assembly secured to the second end of the flexible tube.

3. The system of claim 1, wherein the light assembly includes a power source.

4. The system of claim 3, wherein the light source is a light emitting diode.

5. The system of claim 3, wherein the light source includes a plurality of light emitting diodes.

6. The system of claim 3, wherein the power source includes a battery.

7. The system of claim 3, wherein the light assembly includes an interrupter disposed between the light source and the power source.

8. The system of claim 1, wherein the switch assembly includes a pressure switch.

9. The system of claim 1, wherein the second end of the flexible tube includes is rounded.

10. The system of claim 1, wherein the second end of the flexible tube includes a cap.

11. The system of claim 1, wherein the first end of the flexible tube is open.

12. The system of claim 1, wherein the second end of the flexible tube is closed.

13. A method of trans-oral insertion of an anvil assembly into a patient, the method comprising:
   activating a light source of a light assembly disposed within a first end of a flexible tube of a delivery system such that a light emanates from the first end of the flexible tube, the light assembly including a light source and a switch assembly for activating the light source;
   inserting the first end of the flexible tube into a mouth and down an esophagus of a patient and into a stomach of the patient;
   viewing the light emanating from the first end of the flexible tube within the stomach of the patient;

creating an incision in the stomach of the patient in proximity to the light emanating from the first end of the flexible tube; and receiving the first end of the flexible tube through the incision in the stomach.

14. The method of claim 13, further including securing an anvil assembly to the flexible tube.

15. The method of claim 13, wherein activating the light source includes squeezing the flexible tube to toggle a pressure switch of the switch assembly to an on position.

16. The method of claim 13, wherein activating the light source includes removing an interrupter from the light assembly.

\* \* \* \* \*